United States Patent

Zink et al.

[11] Patent Number: 4,555,569
[45] Date of Patent: Nov. 26, 1985

[54] CHROMOGENIC QUINAZOLINES

[75] Inventors: Rudolf Zink, Therwil; Ian J. Fletcher, Magden, both of Switzerland

[73] Assignee: Ciba-Geigy Corporation, Ardsley, N.Y.

[21] Appl. No.: 623,687

[22] Filed: Jun. 22, 1984

[30] Foreign Application Priority Data

Jun. 28, 1983 [CH] Switzerland ............... 3522/83

[51] Int. Cl.$^4$ ............... C07D 403/02; C07D 413/02
[52] U.S. Cl. ............... 544/105; 544/6; 544/62; 544/70; 544/116; 544/119; 544/230; 544/284; 427/151
[58] Field of Search ............... 544/6, 62, 70, 116, 544/119, 230, 284

[56] References Cited

U.S. PATENT DOCUMENTS 4,435,003 3/1984 Fletcher ............... 282/27.5

Primary Examiner—Robert W. Ramsuer
Attorney, Agent, or Firm—Edward McC. Roberts; Kevin T. Mansfield; Irving M. Fishman

[57] ABSTRACT

The invention relates to chromogenic quinazolines of the formula

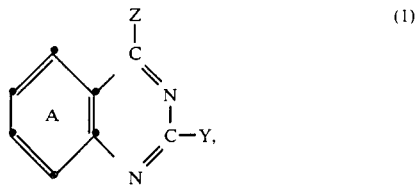

(1)

wherein

Y is a polycyclic non-aromatic heterocyclic radical which is attached to the quinazoline moiety through a fused benzene nucleus and is unsubstituted or substituted, and Z is hydrogen, R, $-OR_1$, $-SR_1$ or $-NR_2R_3$, wherein R and $R_1$ are each alkyl which is unsubstituted or substituted by cyano or lower alkoxy, or are cycloalkyl, unsubstituted or substituted aryl or aralkyl or an unsubstituted or substituted heterocyclic radical, and $R_1$ can also be haloalkyl, $R_2$ and $R_3$, each independently of the other, are hydrogen, alkyl which is unsubstituted or substituted by halogen, hydroxy, cyano or lower alkoxy, or are cycloalkyl, phenyl, benzyl, or phenyl or benzyl which are each substituted by halogen, nitro, cyano, lower alkyl, lower alkoxy or lower alkoxycarbonyl, and $R_2$ can also be acyl; or $R_2$ and $R_3$, together with the nitrogen atom to which they are attached, are a 5- or 6-membered heterocyclic radical, and the ring A is unsubstituted or substituted by halogen, cyano, nitro, lower alkyl, lower alkoxy or lower alkoxycarbonyl.

These compounds are particularly suitable color formers in pressure-sensitive or heat-sensitive recording materials and produce strong yellow or orange colorations of excellent fastness to light and sublimation.

14 Claims, No Drawings

CHROMOGENIC QUINAZOLINES

The present invention relates to chromogenic quinazolines, to the preparation thereof, and to the use of these compounds as colour formers in pressure-sensitive or heat-sensitive recording materials.

The novel chromogenic quinazolines have the general formula

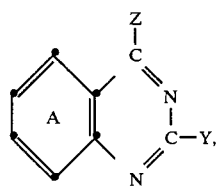
(1)

wherein
Y is a polycyclic non-aromatic heterocyclic radical which is attached to the quinazoline moiety through a fused benzene nucleus and is unsubstituted or substituted, and
Z is hydrogen, R, $-OR_1$, $-SR_1$ or $-NR_2R_3$, wherein R and $R_1$ are each alkyl which contains not more than 12 carbon atoms and is unsubstituted or substituted by cyano or lower alkoxy, or are cycloalkyl, unsubstituted or substituted aryl or aralkyl or an unsubstituted or substituted heterocyclic radical, and $R_1$ can also be $C_2$-$C_6$haloalkyl,
$R_2$ and $R_3$, each independently of the other, are hydrogen, alkyl which contains not more than 12 carbon atoms and is unsubstituted or substituted by halogen, hydroxy, cyano or lower alkoxy, or are cycloalkyl, phenyl, benzyl, or phenyl or benzyl which are each substituted by halogen, nitro, cyano, lower alkyl, lower alkoxy or lower alkoxycarbonyl, and $R_2$ can also be $C_1$-$C_{12}$acyl; or $R_2$ and $R_3$, together with the nitrogen atom to which they are attached, are of 5- or 6-membered, preferably saturated heterocyclic radical, and the ring A is unsubstituted or substituted by halogen, cyano, nitro, lower alkyl, lower alkoxy or lower alkoxycarbonyl.

In the definition of the radicals of the quinazolines, lower alkyl and lower alkoxy normally denote those groups or moieties which contain 1 to 5, preferably 1 to 3, carbon atoms.

Examples of lower alkyl groups are methyl, ethyl, n-propyl, isopropyl, n-butyl, sec-butyl, tert-butyl or amyl; and lower alkoxy groups are for example methoxy, ethoxy or isopropoxy.

The term "aryl" signifies preferably phenyl. Acyl is preferably formyl or lower alkylcarbonyl, for example acetyl or propionyl, or is benzoyl. Further acyl radicals are lower alkysulfonyl, e.g. methylsulfonyl or ethylsulfonyl, and phenylsulfonyl. Phenyl, benzoyl and phenylsulfonyl can be substituted by halogen, methyl, methoxy or ethoxy.

Halogen is for example fluorine, bromine or, preferably, chlorine.

Alkyl groups R, $R_1$, $R_2$ and $R_3$ may be straight chain or branched. Examples of such alkyl groups are: methyl, ethyl, n-propyl, isopropyl, n-butyl, sec-butyl, amyl, n-hexyl, 2-ethyl-hexyl, isooctyl, n-octyl, decyl or n-dodecyl.

Substituted alkyl groups R, $R_1$,$R_2$ and $R_3$ are preferably cyanoalkyl or alkoxyalkyl, each preferably containing a total of 2 to 6 carbon atoms, e.g. β-cyanoethyl, β-methoxyethyl or β-ethoxyethyl. $R_1$ as haloalkyl can be for example γ-chloropropyl or, preferably, β-chloroethyl.

The acyl radical $R_2$ is for example formyl, lower alkylcarbonyl or benzoyl, and is preferably acetyl or propionyl. Benzoyl can be substituted in the benzene ring by halogen, methyl or methoxy.

R, $R_1$, $R_2$ and $R_3$ as cycloalkyl are for example cyclopentyl or, preferably, cyclohexyl.

R and $R_1$ as aralkyl are normally phenylethyl or, preferably, benzyl, and aryl is preferably naphthyl, diphenyl and, most preferably, phenyl. The aralkyl and aryl radicals can be substituted by halogen, cyano, nitro, lower alkyl, lower alkoxy, lower alkoxycarbonyl or lower alkylcarbonyl.

Preferred substituents in the benzyl and phenyl moiety of the radicals R, $R_1$, $R_2$ and $R_3$ are e.g. halogen, cyano, methyl, methoxy or carbomethoxy. Examples of such araliphatic and aromatic radicals are: methylbenzyl, chlorobenzyl, cyanophenyl, tolyl, xylyl, chlorophenyl, methoxyphenyl or carbomethoxyphenyl.

A heterocyclic radical R or $R_1$ is preferably a 5- or 6-membered heterocyclic ring system of aromatic character which preferably contains oxygen, sulfur or nitrogen. Examples of such heterocyclic ring systems are thienyl, furyl, pyrrolyl, pyrazolyl, imidazolyl or, preferably, pyridyl. These heterocyclic radicals can be substituted, preferably by halogen, cyano, lower alkyl, lower alkoxy or lower alkoxycarbonyl. Preferred heterocyclic radicals R and $R_1$ are 2-furyl, 2-thienyl and, in particular, 2-, 3- or 4-pyridyl.

A heterocyclic radical $-NR_2R_3$ is for example pyrrolidino, piperidino, pipecolino, morpholino, thiomorpholino or piperazino such as N-methylpiperazino. Preferred saturated heterocyclic radicals $-NR_2R_3$ are pyrrolidino, piperidino or morpholino.

In formula (1) Z is preferably the $-OR_1$ radical.

Suitable polycyclic non-aromatic compounds for the radical Y are e.g. N-unsubstituted or N-substituted indolines, tetrahydrocarbazoles, dihydro- or tetrahydroquinolines, dibenzylimides or benzomorpholines. Y is attached to the quinazoline moiety through the fused benzene ring of the heterocyclic ring systems referred to above. Preferred radicals Y are the indoline, tetrahydroquinoline and benzomorpholine radicals.

The polycyclic heterocyclic compounds for the radical Y can also be ring-substituted by one or more C-substituents. Suitable C-substituents are e.g. halogens, hydroxyl, cyano, lower alkyl, lower alkoxy, lower alkoxycarbonyl, $C_1$-$C_8$acyl, preferably lower alkanoyl, alkylene, cycloalkyl, benzyl or phenyl; and N-substituents are e.g. $C_1$-$C_{12}$alkyl, $C_3$-$C_{12}$alkenyl or benzyl, each of which can also be substituted e.g. by cyano, halogen, hydroxyl, lower alkyl, lower alkoxy or lower alkoxycarbonyl. The alkyl and alkenyl radicals can be straight chain or branched. Examples of alkyl radicals are methyl, ethyl, n-propyl, isopropyl, n-butyl, sec-butyl, amyl, n-hexyl, 2-ethyl-hexyl, isooctyl, n-octyl, decyl or n-dodecyl; and alkenyl is for example allyl, 2-methallyl, 2-ethallyl, 2-butenyl or octenyl.

The ring A is preferably not further substituted. If it does contain substituents, then it is preferably mono- or disubstituted by halogen, cyano, lower alkyl or lower alkoxy, e.g. by cyano, chlorine, methyl or methoxy.

Interesting chromogenic quinazolines are those of the formula

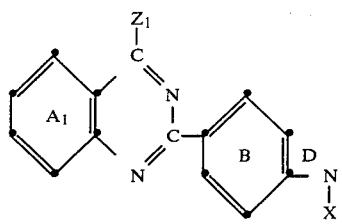

(2)

wherein

X is hydrogen, alkyl which contains not more than 8 carbon atoms and is unsubstituted or substituted by halogen, cyano or lower alkoxy, or is cycloalkyl or benzyl, $Z_1$ is hydrogen, $R_4$, $-OR_4$, $-SR_4$ or $-NR_5R_6$, wherein $R_4$ is alkyl which contains not more than 8 carbon atoms and is unsubstituted or substituted by lower alkoxy, or is cyclohexyl, phenyl, naphthyl, benzyl, or phenyl or benzyl which are substituted by halogen, cyano, lower alkyl, lower alkoxy or lower alkoxycarbonyl, $R_5$ and $R_6$, each independently of the other, are hydrogen, lower alkyl, phenyl, lower alkylphenyl, lower alkoxyphenyl or benzyl, and $R_5$ can also be lower alkylcarbonyl, lower alkylsulfonyl, benzoyl or phenylsulfonyl, or $R_5$ and $R_6$ together with the nitrogen atom to which they are attached are pyrrolidino, piperidino or morpholino, and the rings $A_1$ and B, each independently of the other, are unsubstituted or substituted by cyano, halogen, lower alkyl, e.g. methyl, or lower alkoxy, e.g. methoxy, and the ring D is a hydrogenated 5- or 6-membered N-heterocyclic ring system which may contain a further hetero atom, e.g. oxygen, sulfur or nitrogen, as ring member, and is unsubstituted or C-substituted by one or —depending on the substituents—more of the same or different substituents selected from the group consisting of halogen, cyano, hydroxyl, lower alkyl, lower alkoxy, $C_5$-$C_6$cycloalkyl, benzyl and $C_3$-$C_6$alkylene.

Preferred quinazoline compounds of the formula (2) are those in which $Z_1$ is $-OR_4$. $R_4$ is preferably lower alkyl, benzyl or, most preferably, phenyl. X is preferably lower alkyl, benzyl or β-cyanoethyl. The ring D is preferably 6-membered and C-substituted in particular by 1, 2 or 3 methyl groups. The rings $A_1$ and B are preferably unsubstituted. However, the ring B can advantageously contain a methyl group.

Particularly interesting quinazolines are those of the formula

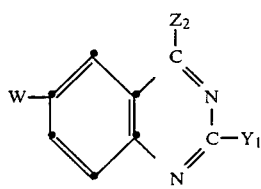

(3)

wherein $Z_2$ is hydrogen, $R_7$, $-OR_7$, $-SR_7$ or $-NR_8R_9$, $R_7$ is lower alkyl, lower alkoxy-lower alkyl, cyclohexyl, phenyl, naphthyl, benzyl, or phenyl which is substituted by halogen, cyano, methyl or methoxy, $R_8$ and $R_9$, each independently of the other, are hydrogen, lower alkyl, phenyl or benzyl, and $R_8$ is also lower alkylcarbonyl or benzoyl, W is halogen, methyl, methoxy or, preferably, hydrogen, and $Y_1$ is a 5-indolinyl radical of the formula

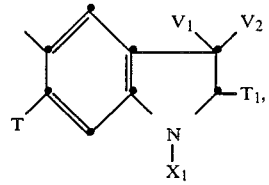

(3a)

a tetrahydroquinolinyl radical of the formula

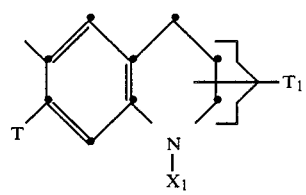

(3b)

a tetrahydroquinolinyl radical of the formula

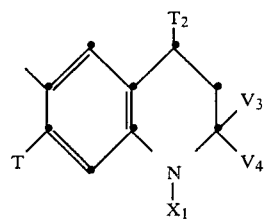

(3c)

or a benzomorpholino radical of the formula

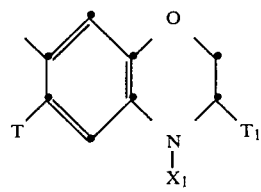

(3d)

$X_1$ is hydrogen, $C_1$-$C_8$alkyl, $C_2$-$C_6$alkoxyalkyl, β-cyanoethyl or benzyl, T is hydrogen, halogen, lower alkyl, lower alkoxy, $C_1$-$C_4$acylamino or phenyl, $T_1$ and $T_2$ are each hydrogen, halogen, hydroxy, lower alkyl or lower alkoxy, and $V_1$, $V_2$, $V_3$ and $V_4$ are each hydrogen, lower alkyl, cycloalkyl or benzyl, or ($V_1$ and $V_2$) or ($V_3$ and $V_4$) are each together alkylene.

In formula (3), $R_7$, $R_8$ and $R_9$ are preferably lower alkyl, benzyl or phenyl. $Z_2$ is preferably $-OR_7$.

The N-substituent $X_1$ is preferably benzyl, β-cyanoethyl or $C_1$-$C_8$alkyl, e.g. n-octyl, n-butyl, isopropyl or, preferably, methyl or ethyl.

$Y_1$ is preferably the tetrahydroquinoline radical of the formula (3c). T is preferably hydrogen or methyl. $T_1$ is preferably hydrogen, methyl, hydroxyl or chlorine. $T_2$ is preferably hydrogen, methyl or ethyl. $V_1$ and $V_2$ are preferably hydrogen or methyl. $V_3$ and $V_4$ are preferably each lower alkyl and most preferably are each methyl.

If ($V_1$ and $V_2$) or ($V_3$ and $V_4$) together are alkylene, then they contain preferably 4 or 5 carbon atoms and, together with the carbon atom to which they are attached, form a cyclopentane or cyclohexane ring. W is preferably hydrogen, halogen or lower alkoxy, e.g. chlorine or methoxy.

Particularly preferred quinazolines are those of the formula

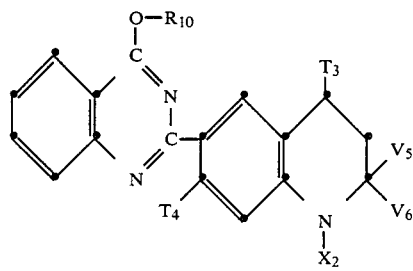

(4)

wherein
$R_{10}$ is lower alkyl, benzyl or preferably phenyl,
$X_2$ is $C_1$-$C_8$alkyl, $\beta$-cyanoethyl or benzyl,
$T_3$, $V_5$ and $V_6$ are each lower alkyl, preferably methyl or ethyl, and
$T_4$ is hydrogen or methyl.

The quinazoline compounds of the formula (1), wherein Z is $-OR_1$, $-SR_1$ or $-NR_2R_3$, are prepared by reacting a 4-haloquinazoline of the formula

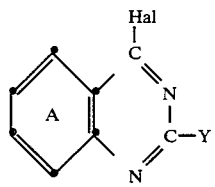

(5)

wherein A and Y have the given meanings and Hal is halogen, e.g. bromine, fluorine or preferably chlorine, with a compound of the formula

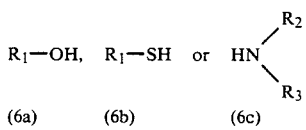

wherein $R_1$, $R_2$ and $R_3$ have the given meanings.

The reaction of the compound of the formula (5) with the compound of formula (6a), (6b) or (6c) is conveniently carried out in the presence of an acid acceptor, e.g. an alkali metal hydroxide, alkali metal carbonate or a tertiary nitrogen base, e.g. pyridine or a trialkylamine, and preferably also in the presence of a quaternary ammonium salt, e.g. tetrabutylammonium bromide, optionally in an organic solvent or in an aqueous-organic two-phase medium, and at reflux temperature.

Suitable solvents are for example cycloaliphatic or aromatic hydrocarbons such as cyclohexane, benzene, toluene or xylene; chlorinated hydrocarbons such as chloroform, ethylene chloride or a chlorobenzene, preferably dichlorobenzene; ethers such as diethyl ether or glycol dimethyl ether; cyclic ethers such as dioxan or tetrahydrofuran; and dimethylformamide, diethylformamide, dimethylsulfoxide or acetonitrile.

One method of preparing compounds of formula (1), wherein Z is hydrogen, comprises dehalogenating the 4-haloquinazoline of the formula (5), under alkaline conditions, to replace the halogen atom by hydrogen. This dehalogenation is carried out e.g. in accordance with J. Chem. Soc. 1962, 561–572, using toluene-p-sulfonyl hydrazide, and decomposing the 4-(N-toluene-p-sulfonyl hydrazino)quinoline with alkali, e.g. sodium hydroxide, preferably in ethylene glycol or ethylene glycol monomethyl ether.

The starting materials of the formula (5) can be prepared by reacting e.g. a 2-aminobenzamide of the formula

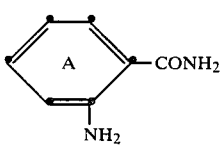

(7)

with an aldehyde of the formula

 (8)

to give a 1,2,3,4-tetrahydroquinazol-4-one of the formula

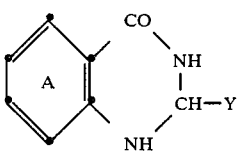

(9)

oxidising this compound to a compound of the formula

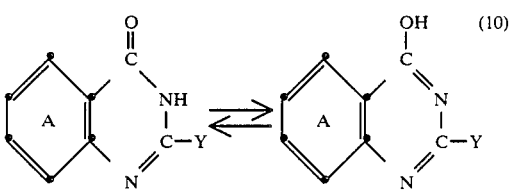

(10)

then replacing the hydroxyl group at the heterocyclic ring of the quinazoline system by a halogen atom, e.g. with phosphoroxy chloride in dichlorobenzene or with thionyl chloride in dimethylformamide, to give the starting material of the formula (5), the 4-haloquinazoline can be further used without being isolated.

The oxidation of the reaction products of the formula (9) to the 4-quinazolones of the formula (10) is carried out with oxidising agents. Suitable oxidising agents are e.g. chromates, bichromates, chlorates, chlorites, peroxides, e.g. hydrogen peroxide, manganese dioxide, lead dioxide, molecular oxygen, air, perborates, permanganates, nitrites, chlorine, bromine and, in particular, chloranil or bisulfites.

The best results with respect to yield and purity of the 4-quinazolones are obtained with chloranil as preferred oxidising agent. The oxidation with sodium bisulfite affords ecological advantages. Following the procedure described in Synthesis 1981, (1), 35, quinazolones of the formula (10) are obtained in good yield and purity using this oxidising agent.

A preferred process for the preparation of compounds of the formula (1), wherein Z has the meaning of R, comprises reacting a ketoamido compound of the formula

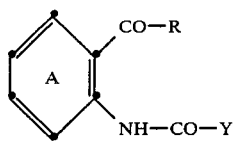

wherein A, R and Y have the given meanings, with a solution of ammonia in alcohol, preferably in methanol, to give a quinazoline of the formula

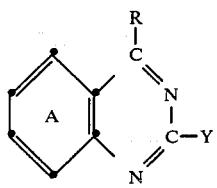

The reaction of the ketoamido compound of the formula (11) with the ammonia solution can be carried out at a temperature in the range from 80° to 200° C., preferably from 100° to 180° C. Compounds of the formula (11) can be prepared according to A. Bischler and D. Barad, Ber., 25, 3080 (1982) and F. J. Howell, Ber. 26, 1384 (1893), by acylating the corresponding ketoamino compounds with the desired acid anhydrides or acid halides.

The quinazolines of the formula (1) to (4) are normally colourless or, at most, faintly coloured. When these colour formers are brought into contact preferably with an acid developer, e.g. an electron acceptor, they produce—depending on the meaning of Y and Z— strong yellow, orange or red shades of excellent fastness to sublimation and light. They are therefore also very useful when combined with one or more other known colour formers, for example 3,3-(bis-aminophenyl)phthalides, 3,3-(bis-indolyl)phthalides, 3-aminophenyl-3-indolylazaphthalides, 3-aminofluoranes, 2,6-diaminofluoranes, leucoauramines, spiropyranes, spirodipyranes, chromenoindoles, chromenopyrazoles, phenoxazines, phenothiazines, 2-aminophenylquinazolines, bisquinazolines, carbazolylmethanes or other triarylmethaneleuco dyes, to give blue, navy blue, grey or black colorations.

The quinazolines of the formulae (1) to (4) exhibit both on phenolic substrates, and especially on clays, an excellent colour intensity and lightfastness. They are suitable in particular as rapidly developing colour formers for use in a heat-sensitive, or especially in a pressure-sensitive, recording material which can also be a copying material. They are distinguished by the property that they have excellent solubility in the capsule oils and exhibit only insignificant loss of colour intensity (CB decline) on exposure in a CB sheet.

A pressure-sensitive material consists, for example, of at least one pair of sheets which contain at least one colour former of the formulae (1) to (4) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay, or acidic organic compounds, for example unsubstituted or ring-substituted phenols, salicylic acid or salicylates and their metal salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are acid-activated bentonite, zinc salicylates, or the condensation products of p-substituted phenols with formaldehyde. These last mentioned compounds may also contain zinc.

The developers may also be used in admixture with other basically inert or almost inert pigments or with other auxiliaries such as silica gel or UV absorbers, e.g. 2-(2-hydroxyphenyl)-benzotriazoles. Examples of such pigments are: talcum, titanium dioxide, zinc oxide, chalk, clays such as kaolin, as well as organic pigments, e.g. urea/formaldehyde condensates (BET surface area: 2–75 m$^2$/g) or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomblike structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, diphenylalkane, naphthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsules walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specifications Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (4) can be used for the production of a wide variety of known kinds of pressure-sensitive copying material. The various systems differ substantially from one another in the arrangement of the capsules, of the colour reactants, and of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (4) can also be employed as colour formers in a thermoreactive recording material. This recording material usually contains at least one carrier, one colour former, one electron acceptor, and optionally also a binder, and/or wax.

Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) information can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer.

Another possibility comprises in dispersing both the colour former and the developer in one layer. By means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, methylene bis-(2-methylphenyol), 4-hydroxydiphenyl ether, α-naphthol, β-naphthol, methyl 4-hydroxybenzoate, 4-hydroxyacetophenone, 2,2'-dihydroxydiphenyl, 4,4'-isopropylidenediphenol, 4,4'-isopropylidene-bis-(2-methylphenol), 4,4'-bis-(hydroxyphenyl) valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the quinazolines and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carbomethylcellulose, polyacrylamide, polyvinyl pyrrolidone, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, steary amide, phthalic anhydride, metal stearates, dimethyl terepthalate, phthalonitrile or other appropriate fusible products which induce the simultaneous melting of the colour former and the developer. Thermographic recording materials preferably contain waxes, e.g. carnauba wax, montan wax, paraffin wax, polyethylene wax, condensates or higher fatty acid amides and formaldehyde, or condensates of higher fatty acids and ethylenediamine.

The invention is illustrated by the following Examples, in which percentages are by weight, unless otherwise indicated.

EXAMPLE 1

19 g of the quinazolone of the formula

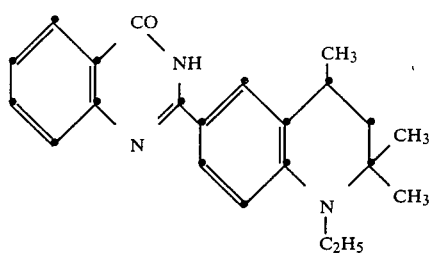

(i)

are dissolved at 150° C. in 90 g of 1,2-dichlorobenzene. The solution is then cooled to 95° C. and 9 g of phosphoroxy trichloride are added dropwise at this temperature over 30 minutes. The reaction mixture is then stirred for 1 hour at 90°–95° C. The red solution of the 4-chloro-2-tetrahydroquinolinylquinazoline compound of the formula

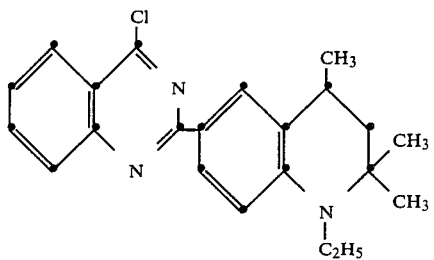

(ii)

is poured into a suspension consisting of 5.2 g of phenol, 2.2 g of tetrabutylammonium bromide and 35 g of a 50% aqueous solution of sodium hydroxide over the course of 15 minutes, whereupon the temperature rises to 110° C. The reaction mixture is stirred for 1 hour at 100°–110° C. and the 1,2-dichlorobenzene is removed by steam distillation. The precipitated product is dissolved in toluene, with heating, and the hot toluene solution is filtered over activated carbon. The product crystallises from the cooled solution and is isolated by filtration and dried, affording 20 g of a compound of the formula

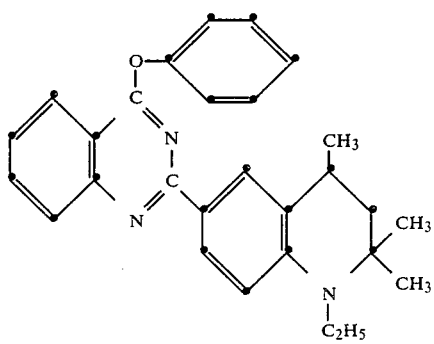

(21)

with a melting point of 145°–147° C.

On acid clay this colour former develops a reddish yellow shade with good fastness to light and sublimation. $\lambda_{max}=477$ nm.

The starting quinazolone of the formula (i) used in this Example can be prepared as follows:

23.1 g of N-ethyl-2,2,4-trimethyltetrahydroquinoline-6-aldehyde are dissolved in 150 ml of ethanol. To this solution are added 13.6 g of anthranilamide and 4 ml of 10% sulfuric acid and the reaction mixture is heated to 60° C. and kept at this temperature for 1 hour. The product is oxidised by the dropwise addition of 69 g of a 40% aqueous solution of sodium bisulfite and subsequently stirring the reaction mixture for 2 hours at reflux temperature. After cooling to room temperature, the precipitate is isolated by filtration, washed with ethanol and dried. Yield: 19 g of the quinazolone compound of the formula (i) with a melting point of 215°–219° C. The colour formers of the formula

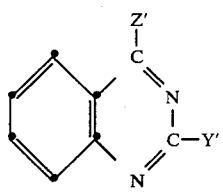

(22)

are obtained in the same manner as described in this Example using the corresponding starting materials.

TABLE

| Example | Z' | Y' | $\lambda_{max}$ on acid clay in nm | Colour |
|---|---|---|---|---|
| 2 | —OCH$_3$ | ![structure with CH$_3$, CH$_3$, CH$_3$, N-C$_2$H$_5$] | 467 | yellow |
| 3 | —O—⬡ | ![structure with CH$_3$, CH$_3$, CH$_3$, N-C$_2$H$_4$CN] m.p. 175–181° C. | 451 | yellow |
| 4 | —O—⬡ | ![structure with CH$_3$, CH$_3$, CH$_3$, N-CH$_2$-⬡] | 476 | yellow |
| 5 | —O—⬡ | ![structure with CH$_3$, CH$_3$, CH$_3$, CH$_3$] m.p. 113–128° C. | 476 | golden yellow |
| 6 | —O—CH$_2$—⬡ | ![structure with CH$_3$, CH$_3$, CH$_3$, CH$_3$] m.p. 164–166° C. | 468 | yellow |

TABLE-continued

| Example | Z' | Y' | λmax on acid clay in nm | Colour |
|---|---|---|---|---|
| 7 | —O—⟨phenyl⟩ | (structure with CH₃ groups, N-C₂H₅, CH₃) m.p. 139–140° C. | 482 | golden yellow |
| 8 | —O—⟨phenyl⟩ | (structure with CH₃, N-C₂H₅) m.p. 103–106° C. | 480 | golden yellow |
| 9 | —O—⟨phenyl⟩ | (structure with CH₃, N-CH₃) | 483 | orange |
| 10 | —O—⟨phenyl⟩ | (structure with O, CH₃, N-C₂H₅) | 480 | golden yellow |

EXAMPLE 11

Preparation of a pressure-sensitive-copying paper.

A solution of 3 g of the quinazoline of the formula (21) in 80 g of partially hydrogenated terphenyl and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or type-writer and a strong reddish yellow copy of excellent fastness to sublimation and light develops immediately on the sheet coated with the developer.

Corresponding strong yellow or orange copies which are fast to sublimation and light are also obtained by using any of the other colour formers of Examples 2 to 10.

EXAMPLE 12

Following the procedure as described in Example 11, but replacing the quinazoline of the formula (21) by a mixture of the following composition:
1.2 g of 3,3-bis-(4'-dimethylaminophenyl)-6-dimethylaminophthalide,
1.2 g of N-butylcarbazol-3-yl-bis-(4'-N-methyl-N-phenylaminophenyl)methane,
1.2 g of quinazoline of the formula (21) and
0.4 g of 3,3-bis-(N-n-octyl-2'-methylindol-3'-yl)phthalide, there is obtained a pressure-sensitive recording material which gives a strong and lightfast black copy by writing by hand or typewriter.

EXAMPLE 13

1 g of the quinazoline of the formula (21) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of apper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and a strong reddish yellow copy which is fast to sublimation and light develops immediately on the sheet coated with the colour former.

EXAMPLE 14

Preparation of a heat-sensitive recording material.

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to particle size of about 5 μm. In a second ball mill, 6 g of the quinazoline of the formula (21), 3 g of a 88% hydrolysed polyvinyl alcohol and 60 ml of water are ground to particle size of about 3 μm.

Both dispersions are mixed and applied to paper to a dry coating weight of 5.5 g/m². A strong yellow colour of excellent fastness to light and sublimation is produced by contacting the paper with a heated ball-point pen.

Strong yellow colour which is fast to sublimation and light is obtained by contacting the paper with a heated ball-point pen.

EXAMPLE 15

In a ball mill, 2.7 g of the quinazoline of the formula (21), 24 g of N-phenyl-N'-(1-hydroxy-2,2,2-trichloroethyl)urea, 16 g of stearylamide, 59 g of an 88% hydrolysed polyvinyl alcohol and 58 ml of water are ground to a particle size of 2–5 μm. This suspension is applied to a sheet of paper to a dry coating weight of 5.5 g/m².

What is claimed is:

1. A chromogenic quinazoline of the formula

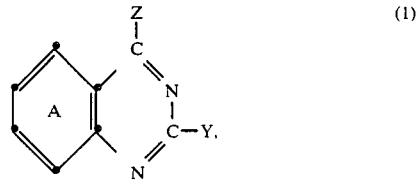

(1)

wherein
- Y is a polycyclic non-aromatic heterocyclic radical selected from an indoline, tetrahydroquinoline or benzomorpholine radical which is attached to the quinazoline moiety through a fused benzene nucleus and is unsubstituted or substituted, and
- Z is hydrogen, R, $-OR_1$, $-SR_1$ or $-NR_2R_3$, wherein
- R and $R_1$ are each alkyl which contains not more than 12 carbon atoms and is unsubstituted or substituted by cyano or lower alkoxy, or are cycloalkyl, unsubstituted or substituted aryl or aralkyl or an unsubstituted or substituted heterocyclic radical, and $R_1$ is also $C_2$–$C_6$haloalkyl, $R_2$ and $R_3$, each independently of the other, are hydrogen, alkyl which contains not more than 12 carbon atoms and is unsubstituted or substituted by halogen, hydroxy, cyano or lower alkoxy, or are cycloalkyl, phenyl, benzyl, or phenyl or benzyl which are each substituted by halogen, nitro, cyano, lower alkyl, lower alkoxy or lower alkoxycarbonyl, and $R_2$ is also $C_1$–$C_{12}$acyl; or $R_2$ and $R_3$, together with the nitrogen atom to which they are attached, are a 5- or 6-membered, saturated heterocyclic radical, and the ring A is unsubstituted or substituted by halogen, cyano, nitro, lower alkyl, lower alkoxy or lower alkoxycarbonyl.

2. A quinazoline according to claim 1, wherein each of R and $R_1$ is phenyl, naphthyl, diphenyl, benzyl or phenylethyl, each of which is unsubstituted or substituted by halogen, cyano, nitro, lower alkyl, lower alkoxy, lower alkoxycarbonyl or lower alkylcarbonyl.

3. A quinazoline according to claim 1, wherein each of R and $R_1$ is a 5- or 6-membered heterocyclic radical of aromatic character which is unsubstituted or substituted by halogen, cyano, lower alkyl, lower alkoxy or lower alkoxycarbonyl.

4. A quinazoline according to claim 1, wherein Z is $-OR_1$.

5. A quinazoline according to claim 1, of the formula

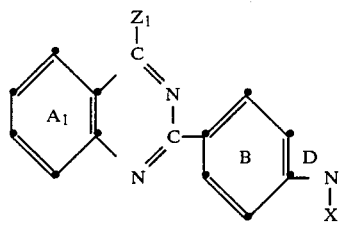

(2)

wherein

X is hydrogen, alkyl which contains not more than 8 carbon atoms and is unsubstituted or substituted by halogen, cyano or lower alkoxy, or is cycloalkyl or benzyl, $Z_1$ is hydrogen, $R_4$, $-OR_4$, $-SR_4$ or $-NR_5R_6$, wherein $R_4$ is alkyl which contains not more than 8 carbon atoms and is unsubstituted or substituted by lower alkoxy, or is cyclohexyl, phenyl, naphthyl, benzyl, or phenyl or benzyl which are substituted by halogen, cyano, lower alkyl, lower alkoxy or lower alkoxycarbonyl, $R_5$ and $R_6$, each independently of the other, are hydrogen, lower alkyl, phenyl, lower alkylphenyl, lower alkoxyphenyl or benzyl, and $R_5$ is also lower alkylcarbonyl, lower alkylsulfonyl, benzoyl or phenylsulfonyl, or $R_5$ and $R_6$ together with the nitrogen atom to which they are attached are pyrrolidino, piperidino or morpholino, and the rings $A_1$ and B, each independently of the other, are unsubstituted or substituted by cyano, halogen, lower alkyl, or lower alkoxy, and the ring D is hydrogenated 5- or 6-membered N-heterocyclic ring which is unsubstituted or C-substituted by one or more than one of the same or different substituents selected from the group consisting of halogen, cyano, hydroxyl, lower alkyl, lower alkoxy, $C_5$–$C_6$cycloalkyl, benzyl and $C_3$–$C_6$alkylene.

6. A quinazoline according to claim 5, wherein $Z_1$ is $-OR_4$ and $R_4$ is lower alkyl, benzyl or phenyl.

7. A quinazoline according to claim 5, wherein the ring D is 6-membered.

8. A quinazoline according to claim 5, wherein X is lower alkyl, benzyl or β-cyanoethyl.

9. A quinazoline according to claim 1, of the formula

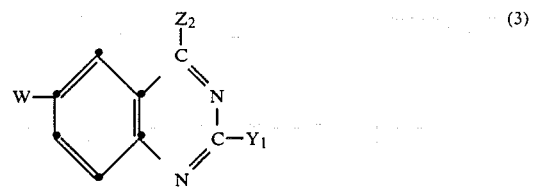

(3)

wherein $Z_2$ is hydrogen, $R_7$, $-OR_7$, $-SR_7$ or $-NR_8R_9$, $R_7$ is lower alkyl, lower alkoxy-lower akyl, cyclohexyl, phenyl, naphthyl, benzyl, or phenyl which is substituted by halogen, cyano, methyl or methoxy, $R_8$ and $R_9$, each independently of the other, are hydrogen, lower alkyl, phenyl or benzyl, and $R_8$ is also lower alkylcarbonyl or benzoyl, W is hydrogen, halogen, methyl or methoxy, and $Y_1$ is a 5-indolinyl radical of the formula

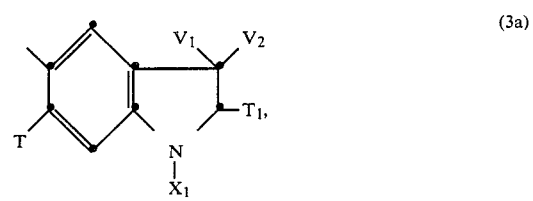

(3a)

a tetrahydroquinolinyl radical of the formula

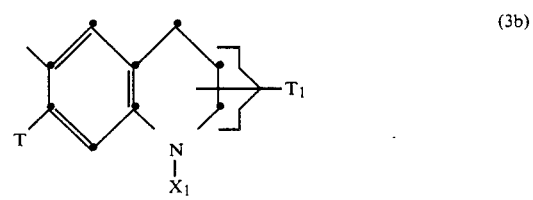

(3b)

a tetrahydroquinolinyl radical of the formula

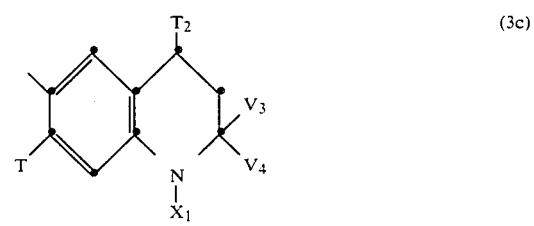

(3c)

or a benzomorpholino radical of the formula

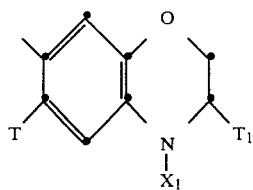
(3d)

$X_1$ is hydrogen, $C_1$-$C_8$alkyl, $C_2$-$C_6$alkoxyalkyl, $\beta$-cyanoethyl or benzyl, T is hydrogen, halogen, lower alkyl, lower alkoxy, $C_1$-$C_4$acylamino or phenyl, $T_1$ and $T_2$ are each hydrogen, halogen, hydroxy, lower alkyl or lower alkoxy, and $V_1$, $V_2$, $V_3$ and $V_4$ are each hydrogen, lower alkyl, cycloalkyl or benzyl, or ($V_1$ and $V_2$) or ($V_3$ and $V_4$) are each together alkylene.

10. A quinazoline according to claim 9, wherein $Y_1$ is the tetrahydroquinoline radical of the formula (3c).

11. A quinazoline according to claim 10, of the formula

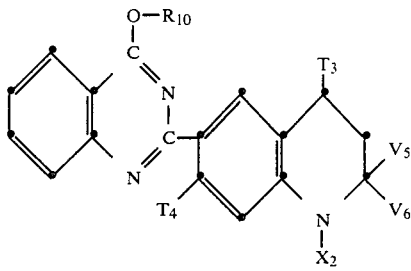
(4)

wherein
$R_{10}$ is lower alkyl, benzyl or phenyl,
$X_2$ is $C_1$-$C_8$alkyl, $\beta$-cyanoethyl or benzyl,
$T_3$, $V_5$ and $V_6$ are each lower alkyl, and
$T_4$ is hydrogen or methyl.

12. A quinazoline according to claim 9, wherein $Y_1$ is the tetrahydroquinolinyl radical of the formula (3b).

13. A quinazoline according to claim 9, wherein $Y_1$ is the benzomorpholino radical of the formula (3d).

14. A quinazoline according to claim 9, wherein $Y_1$ is the 5-indolinyl radical of the formula (3a).

* * * * *